US011046753B2

(12) United States Patent
Gee et al.

(10) Patent No.: US 11,046,753 B2
(45) Date of Patent: Jun. 29, 2021

(54) ANTIBODY COMPOSITION AND BUFFER SYSTEM THEREFOR

(71) Applicant: INNOVA BIOSCIENCES LTD, Cambridge (GB)

(72) Inventors: Nicolas Steven Gee, Cambridge (GB); Bianca Fusetti, Cambridge (GB)

(73) Assignee: INNOVA BIOSCIENCES LTD., Cambridge (GB)

( * ) Notice: Subject to any disclaimer, the term of this patent is extended or adjusted under 35 U.S.C. 154(b) by 0 days.

(21) Appl. No.: 14/894,828

(22) PCT Filed: May 30, 2014

(86) PCT No.: PCT/EP2014/061281
§ 371 (c)(1),
(2) Date: Nov. 30, 2015

(87) PCT Pub. No.: WO2014/191560
PCT Pub. Date: Dec. 4, 2014

(65) Prior Publication Data
US 2016/0122416 A1 May 5, 2016

(30) Foreign Application Priority Data

May 31, 2013 (GB) ..................... 1309759

(51) Int. Cl.
| C07K 16/00 | (2006.01) |
| A61K 49/00 | (2006.01) |
| A61K 47/69 | (2017.01) |
| A61K 47/68 | (2017.01) |
| C07K 1/13 | (2006.01) |
| C07K 1/14 | (2006.01) |

(52) U.S. Cl.
CPC .......... *C07K 16/00* (2013.01); *A61K 47/6843* (2017.08); *A61K 47/6923* (2017.08); *A61K 49/0043* (2013.01); *A61K 49/0045* (2013.01); *A61K 49/0058* (2013.01); *C07K 1/13* (2013.01); *C07K 1/14* (2013.01)

(58) Field of Classification Search
None
See application file for complete search history.

(56) References Cited

U.S. PATENT DOCUMENTS

| 8,492,129 B2 * | 7/2013 | Gee ................. A61K 47/48338 435/174 |
| 2007/0053871 A1 * | 3/2007 | Li ..................... A61K 9/0019 424/85.1 |
| 2012/0237998 A1 * | 9/2012 | Gee .................... B65D 85/84 435/183 |

FOREIGN PATENT DOCUMENTS

| CN | 102089662 | 6/2011 |
| CN | 102250200 | 11/2011 |
| CN | 102788876 | 11/2012 |
| EP | 0516873 A1 | 12/1992 |
| EP | 0988861 A1 | 3/2000 |
| EP | 1977763 | 8/2008 |
| EP | 2380593 | 10/2011 |
| JP | 2008-536917 | 9/2008 |
| JP | 2010-513522 | 4/2010 |
| JP | 2011-241206 | 12/2010 |
| JP | 2011-528106 | 11/2011 |
| JP | 2012-242394 | 12/2012 |
| KR | 20070122554 | 12/2007 |
| WO | 2006112838 | 10/2006 |
| WO | 2007037795 A2 | 4/2007 |
| WO | 2008079290 | 7/2008 |
| WO | 2007/074880 | 6/2009 |
| WO | 2012/123488 | 9/2012 |
| WO | 2011/162210 | 8/2013 |

OTHER PUBLICATIONS

Schägger H, "Tricine-sodium dodecyl sulfate-polyacrylamide gel electrophoresis for the separation of proteins in the range from 1 to 100 kDa," Anal Biochem. Nov. 1, 1987;166(2):368-79.
May 1, 2007, X055134198, Retrieved from the Internet: URL: https://www.luminexcorp.com/prod/groups/public/documents/lmnxcorp/protein-buffers-protocol.pdf.
Ejima, D. et al., "Effective elution of antibodies by arginine and arginine derivatives in affinity column chromatography", Analytical Biochemistry, 2005; 345: 250-257.
Essen, L-O and Skerra, A., "Single-step purification of a bacterially expressed antibody Fv fragment by immobilized metal affinity chromatography in the presence of betaine", Journal of Chromatography A, 1993; 657: 55-61.
https://en.wikipedia.org/wiki/Downstream_processing, Jun. 15, 2018 , 2 pages.
Hermanson GT. Bioconjugate Techniques, Academic Press; San Diego, CA: 1996. pp. 191.
Falconer, et al. "Stabilization of a monoclonal antibody during purification and formulation by addition of basic amino acid excipients," J Chem Technol Biotechnol. Jun. 2011;86: 942-8.

(Continued)

*Primary Examiner* — Yunsoo Kim
(74) *Attorney, Agent, or Firm* — James S. Keddie; Bozicevic, Field & Francis LLP (57) ABSTRACT

A method for conjugating an isolated antibody to a label or derivatisation reagent, which method comprises contacting the antibody with an activated label or activated derivatisation reagent, or contacting the antibody with the label or derivatisation reagent in the presence of an antibody conjugation reagent, in a buffer system which comprises a monocarboxylic acid buffer compound other than glycine, bearing an amine substituent at the alpha or beta position.

25 Claims, 6 Drawing Sheets

(56) References Cited

OTHER PUBLICATIONS

Definition of "derivatization" from Collins English Dictionary online, as displayed at: https://www.collinsdictionary.com/dictionary/english/derivatization retrieved on Jan. 3, 2019.

Kerr, M.A. et al. "Chapter 8 Derivatization of Antibodies and Antigens: Fluorescent Labeling, Biotinylation, Immunogold Derivatives," Immunochemistry Labfax, BIOS Scientific Publishers, 1994, pp. 157-174.

Bjorn MJ, et al. "Evaluation of monoclonal antibodies for the development of breast cancer immunotoxins," Cancer Res. Mar. 1985;45(3):1214-21.

Jhang P, et al. "Novel nitrocellulose membrane substrate for efficient analysis of circulating tumor cells coupled with surface-enhanced Raman scattering imaging," ACS Appl Mater Interfaces. Jan. 8, 2014;6(1):370-6.

Duke-Cohan JS, et al. "Regulation of thymocyte trafficking by Tagap, a GAP domain protein linked to human autoimmunity," Sci Signal. Jun. 12, 2018;11(534).

"MOPS." Wikipedia, Wikimedia Foundation, Jun. 5, 2019, https://en.wikipedia.org/wiki/MOPS.

"HEPES." Wikipedia, Wikimedia Foundation, Aug. 4, 2019, https://en.wikipedia.org/wiki/HEPES.

* cited by examiner

ANTIBODY COMPOSITION AND BUFFER SYSTEM THEREFOR

RELATED APPLICATION INFORMATION

This application is a U.S. National Phase Application submitted under 365 U.S.C. 371 based on International Application No. PCT/EP2014/061281 filed May 30, 2014 (published as WO2014/191560 on Dec. 4, 2014) which claims the benefit of United Kingdom Patent Application 1309759.7 filed May 31, 2013, all of which are hereby incorporated by reference in their entirety.

FIELD OF THE INVENTION

The present invention relates to an antibody composition for use in a conjugation reaction, an antibody isolation kit, a method for conjugating an isolated antibody to a label and a buffer system for use in such a composition, kit or method.

BACKGROUND OF THE INVENTION

All antibodies are made initially in a crude form (e.g. immune serum, ascites fluid, hybridoma tissue culture supernatant). Before use in many basic research and diagnostic applications, antibodies must be purified to remove many (or all) of the contaminating non-antibody proteins and small molecules (e.g. amino acids).

Purification is particularly important if the antibody is to be covalently attached either to a 'label' (e.g. an enzyme, organic dye, fluorescent protein or coloured particle) to create a hybrid reagent, usually referred to as a 'labelled antibody' or 'antibody conjugate' or to a derivatisation reagent for the purpose of introducing new functional groups. The antibody component of a conjugate confers specificity for a particular antigen (e.g. a protein, drug, peptide or biomarker) and the label confers measurability so that the conjugate can be used to detect and quantify the antigen in, for example, western blots, tissue slices, cultured cells, blood samples, urine, and so on.

A key step in antibody purification is the binding of the antibody either to an antigen affinity column or to a column bearing immobilised protein A, protein G, or protein L, which interact with regions of antibodies not directly involved in antigen binding. Purification of antibody on an antigen affinity column is advantageous in that antibodies of irrelevant antigen specificity in the crude sample are not retained by the column. Such methods of affinity purification are robust and reliable and are widely used to purify antibodies from crude samples such as serum, ascites fluid and hybridoma tissue culture supernatant.

Regardless of which approach to purification is used, the column-bound antibody is usually eluted with a low-pH buffer (typically comprising glycine or citric acid) and then quickly neutralised, for example, with Tris buffer, pH 8.0-9.0, to minimise low pH-induced damage of the antibody. (e.g. Thermo Scientific Protein Purification Technical Handbook, ref 1601617 07/08). Elution with low pH glycine or citric acid buffers is popular because of their low cost and because they have good buffering capacity at the pH values required for disruption of antibody-antigen interactions.

Before storage, neutralised purified antibodies are usually (but not always) dialysed against PBS or some other near-neutral-pH buffer. Often other substances (e.g. BSA, sodium azide, detergents) will be added to the dialysed antibody for the purpose of stabilisation or preventing microbial growth.

It is extremely rare when purchasing an antibody from commercial sources to be given information about the dialysis steps used in the purification process. Thus it may be unclear whether buffer components from the purification process remain in the final preparation of antibody. Such considerations are critically important if the antibody is to be labelled, as buffers used to elute affinity columns often cause severe interference in labelling reactions.

Labels of all types are most commonly attached to lysine residues on antibody molecules. For example, NHS esters of organic fluorescent dyes and the popular isothiocyanate derivative of fluorescein (FITC) react with lysine residues. While other conjugation chemistries (e.g. thiol-maleimide) may not obviously involve lysine residues, they are nonetheless nearly always dependent on lysine modification at an earlier step in the conjugation process. For example, lysine-directed heterobifunctional NHS ester derivatisation reagents are commonly used to introduce maleimides and a variety of other functional groups (e.g. protected thiols, azides, iodoacetyl groups) into protein molecules. Carbodiimides, which are used to conjugate antibodies to carboxylated microparticles or nanoparticles, involve the reaction of surface carboxyl groups with lysine residues in antibodies resulting in the formation of amide bonds.

It is well-known that derivatisation or conjugation reactions that involve lysine residues cannot be carried out in the presence of primary amine-containing substances, such as free amino acids. This is because such substances will compete with the lysine residues in the protein. In the case of carbodiimide-mediated reactions (which involves carboxyl to amine coupling) the prior art strongly teaches against the use of additives with either carboxyl or primary amine functionality because of problems of competition.

Thus, popular antibody elution buffers are contraindicated in nearly all types of antibody labelling methods. Neither glycine nor citric acid can be present in carbodiimide-mediated reactions between an antibody and a label because the reaction involves the condensation of an amine and a carboxyl group.

For example, in Bioconjugate Techniques, Hermanson G T, 1995, ISBN 0-12-342336-8, p 102 (and p 117 in the updated 2nd edition, 2008 ISBN 9780123705013) the following advice is given: "Avoid carboxylate- or amine-containing buffers, such as citrate, acetate, glycine, or Tris".

Bangs Labs, tech note 205 with reference to carbodiimide coupling states "Buffers containing free amines, such as Tris or Glycine, should be avoided".

Reactions using carboxyl-containing microspheres are discussed in 'Immobilization of Enzymes and Cells', 2006, ed. Guisan J M, p 223, ISBN 1-58829-290-8) and the following cautionary note given: "Buffers containing free amines, such as Tris of [sic] glycine should be avoided".

A carbodiimide-dependent biotinylation kit (EZ-Link® Amine-PEGn-Biotin, product code 26136) from ThermoFisher states: "Avoid buffers containing primary amines (Tris, glycine, etc.) or carboxyls (acetate, citrate, etc.) because they will quench the reaction".

G Biosciences' procedure for its Carboxyl Coupling Resin warns: "NOTE: For coupling reactions using EDC avoid the use of buffers containing free amines or phosphates as these will interfere with coupling efficiency. Tris, acetate and glycine buffers all readily react with EDC or the coupling intermediate".

Finally, a protocol for use with a carboxylated gold conjugation kit states: Any other amine or carboxyl containing molecules in the protein solution (including protein stabilizers) will compete with the conjugation reaction." (OceanNanotech, product code GCK).

In the case of lysine-directed modification reactions which do not also involve carboxyl modification, citric acid may be tolerated but glycine is always contraindicated e.g. the DyLight® Amine-Reactive Dyes protocol (Thermo Scientific, No 2032.11) states: 'Buffers that contain primary amines (e.g., Tris or glycine) will interfere because they react with the NHS-ester moiety.'

Potentially interfering small molecules such as glycine and citric acid in an antibody sample may be removed by dialysis or desalting before the antibody is used in conjugation reactions. The efficiency of removal of such molecules by dialysis is related to the volume of the antibody sample relative to that of the dialysis buffer, the number of changes of the dialysis buffer, and whether equilibrium is reached before the next buffer change. Such information is almost never known for commercial antibodies.

Unfortunately it is difficult to dialyse/desalt commercial antibodies without significant losses of material, as the antibody typically is purchased in small quantities (e.g. 100 ul at a concentration of around 1 mg antibody/ml). Moreover dilution of the sample can occur during dialysis, perhaps necessitating subsequent antibody concentration steps (resulting in further losses of material) to achieve the minimum concentration required (typically 1 mg/ml) for use in antibody labelling reactions. Dialysis of milligram quantities of antibody is relatively easy, but the process is necessarily slow, and may take 1-2 days if several changes of buffer are required. Dialysis membranes and the large volumes of dialysis buffer that are required at high milligram scales also add to the cost of production.

The present invention aims to provide methods for purifying and/or conjugating antibodies, kits for such methods and antibody compositions which overcome the drawbacks of the prior art.

SUMMARY OF THE INVENTION

Antibody labelling technologies have advanced significantly in the last few years, particularly with regard to process simplification. Multi-step conjugation methods are being replaced by simple one-step processes that require on the part of the operator no particular knowledge of chemistry.

Better integration of antibody purification procedures and labelling reactions are required in order to avoid intervening dialysis steps, which are slow, increase costs, and result in losses of antibody. There is a clear need for a 'conjugation-friendly elution buffer' (CFEB), since the buffers originally adopted by antibody purification scientists are incompatible with most conjugation chemistries. We define here a CFEB as a buffer with a pKa between 1 and 4 that causes no interference in popular conjugation methods (i.e. minimally, reactions of antibodies with carbodiimides, NHS esters, isothiocyanates, maleimides and thiolation reagents).

In a first aspect, the present invention provides an antibody composition for use in a conjugation reaction. The composition comprises an isolated antibody in a buffer system wherein the buffer system comprises a monocarboxylic acid buffer compound other than glycine, bearing an amine substituent at the alpha or beta position.

In a further aspect, the present invention provides use of a buffer comprising a monocarboxylic acid buffer compound other than glycine, bearing an amine substituent at the alpha or beta position for eluting an antibody from a solid phase.

In a further aspect, the present invention provides an antibody isolation kit which comprises a solid phase affinity matrix for binding an antibody and a buffer for eluting the antibody when bound to the affinity matrix, wherein the buffer comprises a monocarboxylic acid buffer compound other than glycine, bearing an amine substituent at the alpha or beta position.

In a further aspect, the present invention provides a method for conjugating an isolated antibody to a label. The method comprises contacting the antibody with the activated label, or label in the presence of an antibody conjugation reagent, in a buffer system which comprises a monocarboxylic acid buffer compound other than glycine, bearing an amine substituent at the alpha or beta position.

It has surprisingly been found that a buffer system comprising a monocarboxylic acid compound bearing an amine substituent at the alpha or beta position may be used in an antibody conjugation reaction. Such a buffer system may be used in both antibody purification procedures and in conjugation reactions thereby avoiding the need for dialysis steps which are undesirable.

To determine the degree of interference in carbodiimide reactions of molecules likely to be found in commercial antibodies (e,g. glycine, citric acid, azide), we studied reactions between an antibody and a commercially available carboxylated nanoparticle. We were astonished to find that glycine caused no interference, even at high concentrations. Glycine has both amine and carboxyl functions and is clearly contraindicated in the prior art. We exploited this unexpected finding to develop a new purification kit, the antibody product of which can be used not only in carbodiimide reactions, but also with all other popular conjugation chemistries without the need for a pre-conjugation antibody dialysis step. The invention is described more fully below.

The monocarboxylic acid buffer compound bears an amine substituent at the alpha or beta position and may further comprise one or more other substituents provided that they are not capable of interfering with the conjugation reaction. Typically, if present, the further substituents are one or more non-amine substituents. It is preferred that no further substituents are present on the buffer compound.

Secondary or tertiary amines are preferred as the amine substituent typically because these are less reactive than primary amines in the conjugation reaction. The amine substituent is preferably a quaternary ammonium substituent. One preferred class of compounds particularly suitable as the monocarboxylic acid buffer compound are betaines. Betaines contain the quaternary ammonium substituent. A preferred betaine is N,N,N-trimethylglycine, which is also known as glycine betaine.

The amine substituent of the monocarboxylic acid buffer compound may nevertheless be a primary amine. Where the monocarboxylic acid is a primary amino acid, this may be alanine, beta alanine or 2 amino butyric acid. Typical secondary or tertiary amines include proline, tricine, N-methyl glycine, N,N-dimethylglycine or 2-picolinic acid.

The presence of the amine substituent in the monocarboxylic acid buffer compound depresses the pKa of the carboxyl group by stabilising the carboxylate anion through an electron-withdrawing effect. Typically, the carboxyl group of the monocarboxylic acid buffer compound has a pKa in the range of from 1 to 4, preferably in the range of from 1.5 to 3.5. The amine of the monocarboxylic acid buffer compound has a pKa typically of greater than 8, preferably greater than 9. In a conjugation reaction at pH5 the amine is largely in protonated form so that it is unreactive in the conjugation reaction.

The monocarboxylic acid buffer compound is present in the antibody composition at a concentration of less than 200 mM, preferably less than 100 mM, more preferably less than 50 mM.

In one arrangement, the buffer system further comprises a neutralisation buffer compound having a pKa of greater than 5.5. The neutralising buffer compound may be present in the buffer system as a result of how the antibody has been isolated. This is described in further detail below. The pH of the antibody composition is typically in the range from 5 to 9. The neutralising buffer is preferably present so as to increase the pH of the composition following elution from a solid phase at lower pH. Lengthy exposure to low pH is undesirable for antibody compositions because it may induce damage in the antibody protein.

The buffer system may further comprise a catch buffer compound with a pKa in the range of from 6 to 8. In this arrangement the neutralising buffer compound preferably has a pKa above 8 and is more preferably in the range from 8 to 11. The concentration of the catch buffer compound is preferably less than the concentration of the neutralising buffer compound. The catch buffer is described in further detail below.

In one arrangement, the isolated antibody is conjugated to a label. The label may comprise an enzyme, a fluorescent protein, an organic dye, a coloured particle, biotin, streptavidin or a polymer.

In one arrangement, the buffer system is used as a storage medium for an antibody or antibody conjugate. In this way, antibody compositions may be stored ready for use without the need for a dialysis step prior to use.

Where the buffer system comprising the monocarboxylic acid buffer compound is used for eluting an antibody from a solid phase, the solid phase may be arranged in a column. Typically, the solid phase comprises an affinity matrix for the antibody. The pH of the buffer is typically in the range of from 1.8 to 4.8. Acidic pHs of this sort are needed in order to remove the antibody when specifically-bound to the solid phase.

The neutralisation buffer may be used in the isolation of the antibody so as to avoid pH-induced damage from the relatively acidic elution buffer. The neutralisation buffer may comprise a morpholino, piperizine or N-cyclohexyl compound. Preferably, the neutralisation buffer comprises 2-(N-morpholino)ethanesulfonic acid (MES), 3-(N-morpholino)propanesulfonic acid (MOPS), 3-Morpholino-2-hydroxypropanesulfonic acid (MOPSO), (4-(2-hydroxyethyl)-1-piperazineethanesulfonic acid) (HEPES), 3-[4-(2-Hydroxyethyl)-1-piperazinyl]propanesulfonic acid (EPPS or HEPPS), piperazine-N,N'-bis(2-ethanesulfonic acid) (PIPES), N-(2-Hydroxyethyl)piperazine-N'-(2-hydroxypropanesulfonic acid) (HEPPSO); N-(2-Hydroxyethyl)piperazine-N'-(4-butanesulfonic acid) (HEPBS), N-Cyclohexyl-2-aminoethanesulfonic acid (CHES), N-cyclohexyl-3-aminopropanesulfonic acid (CAPS), 4-(cyclohexylamino)-1-butanesulfonic acid (CABS) or 3-(cyclohexylamino)-2-hydroxyl-1-propanesulfonic acid (CAPSO).

The pH of the neutralisation buffer is preferably above 6. Thus, introduction of the neutralisation buffer in sufficient quantity into a composition comprising eluted antibody at acidic pH will increase the pH to a level in which the antibody is relatively stable.

In some arrangements the neutralisation buffer pH is above 8 and most preferably in the range 8.5 to 11, such as 9 to 9.5. The neutralisation buffer typically has a pKa within one unit of the pH value. Where the neutralisation buffer is above 8, it is preferred to use additionally a catch buffer with a pKa in the range of from 6 to 8. The purpose of the catch buffer is to prevent use of the neutralisation buffer causing the pH of the composition comprising eluted antibody to rise too much. Suitable buffer compounds for use as the catch buffer include MOPS or HEPES. The catch buffer may be added as a solution with a pH typically in the range of from 6 to 8. Alternatively, the catch buffer may be combined with the neutralisation buffer. In this situation the pH of the combined solution typically is well above the pKa of the catch buffer, and typically is greater than pH 8.

The method for conjugating the isolated antibody to the label or the derivatisation reagent comprises contacting the antibody with the activated label or activated derivatisation reagent, or contacting the antibody with the label or derivatisation reagent in the presence of an antibody conjugation reagent in the buffer system. The antibody conjugation reagent, activated label or activated derivatisation reagent typically comprises one or more of the following reactive groups: a carbodiimide, an N-hydroxy succinimide ester, a maleimide, an isothiocyanate or a thiolation reagent. The method for conjugating the isolated antibody to the label is typically carried out at a pH in the range of from 5 to 9. Advantageously, prior to the step of contacting the antibody with the label, the antibody is isolated by a step of eluting the antibody from the solid phase as described herein. According to the present invention, a buffer system for conjugating the isolated antibody to the label comprises the buffer used for the step of eluting the antibody. In this way, there is no need for any buffer exchange step such as the dialysis step.

DETAILED DESCRIPTION

The invention will now be described in further detail, by way of example only, with reference to the following Examples and the attached Figures, in which.

In experiments to determine the degree of interference in conjugation reactions of various substances commonly found in commercial antibodies, we discovered that high concentrations of glycine, contrary to an overwhelming body of evidence in the prior art, do not interfere in a carbodiimide-mediated reaction between an antibody and a carboxylated gold nanoparticle.

The concentrations of the various species in the reactions typically were: antibody, 16.67 nM; antibody lysines, 1 uM (assuming 60 lysines per antibody molecule); EDC, 0.1 mM; and glycine, 50 mM. Thus there is a vast molar excess of glycine over both antibody lysines and EDC and yet the acid and amine groups of glycine do not prevent a productive conjugation reaction between lysine residues on the antibody and carboxyl groups on the gold nanoparticle. EDC was found to be obligatory in this reaction; no conjugate was formed in the absence of the carbodiimide.

The chemical reactivity of a functional group is often related to its pKa* and to pH of the reaction mixture. [*pKa values given below are for a temperature of 25° C.].

The pKa of the carboxyl group in glycine (2.35) is relatively low compared with other comparable aliphatic acids (e.g. acetic acid, pKa 4.76) as a result of the stabilising (electron-withdrawing) effect of the alpha-amino group. Calculations using the Henderson-Hasselbach equation show that the amine group of glycine (pKa 9.8) is almost totally in its unreactive protonated form at pH 5.0, which may partly explain why the amino group of glycine can be tolerated in carbodiimide reactions.

However, the first step in a carbodiimide-mediated reaction involves the reaction of EDC with a carboxyl group, which theory shows is 99.78% ionised (i.e. COO⁻) in glycine at pH 5. As this is the form that attacks protonated carbodiimides in aqueous solution, pKa considerations clearly cannot explain the lack of interference of glycine. Rather, the ionised carboxyl group would be expected to consume EDC, via cycles of carboxyl activation and then either rapid hydrolysis or reaction with any available amines, and would thus interfere with the reaction of the antibody with carboxylated nanoparticles.

In view of the misleading statements in the prior art about the effects of glycine in carbodiimide-mediated antibody-nanoparticle conjugation reactions, we wondered if other amine- and carboxyl-containing substances might have been overlooked as potential conjugation-friendly substances. More importantly, we hoped to identify substances compatible with multiple antibody conjugation technologies, not just those compatible with carbodiimide-mediated reactions.

We focused our testing on organic acids with pKa values of around 1-4, which may be suitable for use as buffers for elution of antibody affinity columns. We also extended our study to include other common antibody additives, and a variety of acids, amino acids and other derivatives to try to understand the mechanism behind the lack of interference of glycine in carbodiimide reactions.

Molecules were tested initially at pH 5 in EDC-mediated reactions with carboxylated gold particles (InnovaCoat GOLD, Innova Biosciences). Potentially interesting molecules from this screening exercise were further evaluated in NHS ester reactions, isothiocyanate reactions and thiolation reactions involving iminothiolane. All of these reactions are widely used in the antibody conjugation field and all would be expected to suffer from interference in the presence of glycine.

The results in the screening with a carbodiimide-mediated reaction are shown in Table Phosphate and sodium azide, common additives in antibodies, caused interference probably by directly reacting with EDC. Tris, a common primary amine-containing neutralisation buffer or storage buffer caused severe interference.

Several amino acids and related molecules showing little or no effect were identified, including alanine, DL-2-aminobutyric acid, betaine (glycine betaine; N,N, N-trimethylglycine), N,N-dimethylglycine, beta-alanine, N-methylglycine (sarcosine), 2-picolinic acid (2-pyridinecarboxylic acid), tricine [(N-tris(hydroxymethyl)methylglycine] and proline.

Other amino acids showed significant interference, including GABA (gamma-amino butyric acid) and nicotinic acid.

Mono-amino acids with two acidic groups (e.g. aspartate) caused severe interference (data not shown).

Other acids (i.e. those lacking amines) which caused severe interference included citric acid, succinic acid, trichloroacetic acid, and 2,4,6-trihydroxybenzoic acid.

Acids causing significant interference but not totally abolishing the conjugation reaction included cyclohexane carboxylic acid, sodium acetate and pivalic acid.

Taken together, these data illuminate the structural features that must be engineered into a CFEB buffer to minimise interference in carbodiimide reactions.

All molecules with one acid function and lacking nitrogen atoms (i.e. lacking primary, secondary or tertiary amine; or lacking a quaternized ammonium ion) caused interference. Molecules with two acid functions caused interference irrespective of whether an amine was also present. Thus the presence of both an amine and a carboxyl group, either of which is expected to be contraindicated in carbodiimide reactions, in some cases, can together actually prevent interference.

It is clear that the position of the amine in relation to the acid (typically carboxyl) group is very important. For compounds showing the least interference, the amine and carboxyl functions are separated by one atom. Some molecules with two intervening atoms were reasonably well tolerated, but with three intervening atoms the compounds cause significant interference.

In GABA, the amino and carboxyl functions are separated by three atoms and the amine does not depress the pKa of the acid (pKa 4.23). Most of the acid groups (85.5%) are in the presumed reactive COO— form at pH 5, compared with an even greater amount in the reactive form (~99.8%) for glycine. However, GABA significantly inhibits the carbodiimide-mediated reaction whereas glycine (pKa 2.3) does not. DL-2 amino butyric acid (pKa 2.29), which is a GABA isomer with the amino and carboxylic functions in close proximity (i.e. 1 atom separation) showed no interference.

Analogous results are seen with the aromatic acid, nicotinic acid, pKa 2.2, which showed partial interference in the carbodiimide reaction whereas its isomer, picolinic acid, with amine nitrogen and carboxyl group (pKa 1.07) in close proximity was without effect.

Thus carboxylic acids in the absence of an amine in close proximity cause interference, especially if they have low pKa values and are significantly ionised at pH 5. TCA (pKa 0.7) is essentially fully ionised at pH 5 and causes severe interference. By contrast, pivalic acid (pKa=5.03, i.e. ~50% ionised at pH 5, in which the chlorine atoms of trichloroacetic are replaced with methyl groups) showed only partial inhibition.

Thus the most parsimonious explanation for the lack of effect of glycine in our carbodiimide reactions in aqueous solution is that the negatively and positively charged centres interact, via hydrogen bonds, forming intramolecular rings leading to a reduction in the reactivity of the carboxyl group. Such interactions must also involve one or more water molecules, as glycine does not form zwitterions in the gas phase. The solution structures of even simple amino acids, such as glycine, are very complex, with several water molecules thought to be involved in stabilising glycine zwitterions (Xu et al. J. Chem. Phys. 119, 10696-10701, 2003).

Generally, in chemistry, the formation of 5- or 6-membered rings tend to be favoured over highly strained 3- or 4-membered rings, or rings with 7 or more atoms. Thus it seems likely that the monocarboxylic compounds which do not interfere in our carbodiimide reaction have charged amine and carboxyls which are able to interact either directly with one another, or indirectly via bridging solvent molecules (or possibly ions), to obtain a low-energy-state 5- or 6-membered rings. However, when the charged groups are more remote (i.e. three atom separation), the intramolecular rings are too large to be thermodynamically favoured and the ionised carboxyl group is free to react with protonated carbodiimides.

Thus any molecules with the key structural feature i.e. amine and carboxyl in close proximity (and lacking other interfering groups) with each group substantially ionised are likely to display low reactivity in a carbodiimide reaction at pH 5. Where the pKa of the carboxyl is sufficiently low (<4), the molecule may also be suitable for elution of antibody columns.

Buffers with the key structural feature may have other applications. For example, picolinic acid (amine pKa 5.52) is a far better buffer than MES (pKa 6.15) at pH values below 5. At these pH values, the amine of 2-picolinic acid will be largely protonated and will thus deactivate the carboxyl group. Interestingly, MES buffer is commonly used in carbodiimide reactions at pH 4.7, despite the fact that MES cannot possibly be an effective buffer at this pH. The use of MES at this pH is perhaps explained by concern over the expected interference of buffers with amine and carboxyl groups.

While glycine can be tolerated in carbodiimide reactions between antibodies and carboxylated particles at around pH 5, the primary amine of glycine is likely to be far more reactive in conjugation reactions carried out at higher pH values (e.g. NHS ester reactions), as the amine group is less likely to be protonated. We reasoned that acid molecules incorporating secondary or tertiary amines, or a quaternised ammonium salt, as opposed to a primary amine (as in glycine), might show reduced interference in lysine-based conjugation reactions carried out at higher pH values, while still suppressing the activity of carboxyl groups in carbodiimide reactions at around pH 5.

Figure 1:
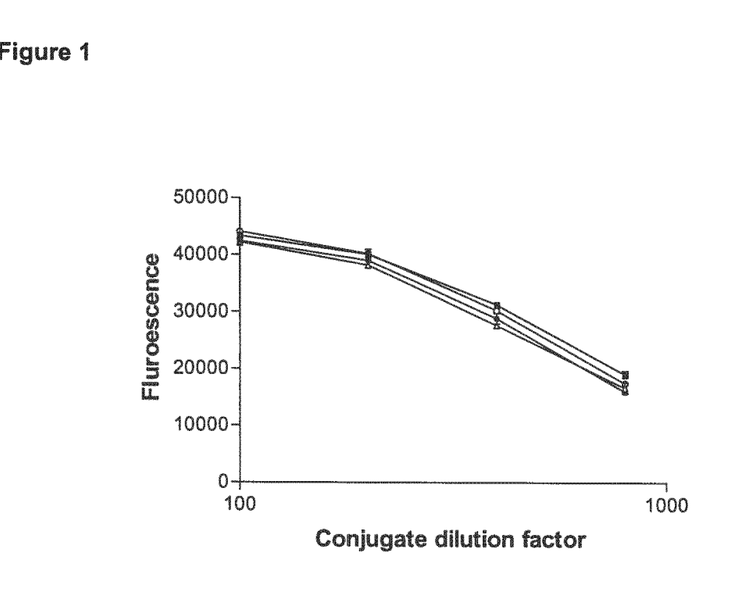
FIG. 1 shows the effect of betaine on a fluorescein conjugation reaction.

Putative CFEBs from the initial testing in carbodiimide-mediation reactions were tested in a commercially available amine-based conjugation technology (Lightning-Link; Innova Biosciences; UK patent Nos. 2446088 & 2467041). Glycine (data not shown) and proline (a secondary amine) caused significant interference at 50 mM concentration in Lightning-Link fluorescein conjugation reactions. 2-picolinic acid showed modest interference. Glycine betaine (a quaternised ammonium salt) and N,N-dimethylglycine (tertiary amine) had little or no effect (% of control values of 98%, 96% at 50 mM concentration, respectively). Full dose-response curves are shown for conjugates prepared in the presence of glycine betaine versus controls without additive (FIG. 1). The figure shows that there is no concentration dependent effect of betaine at various concentrations in a Lightning-Link reaction. Control (no betaine), squares; 1 mM betaine, triangles; 10 mM betaine, open circles; 50 mM betaine, closed circles.

Figure 2:
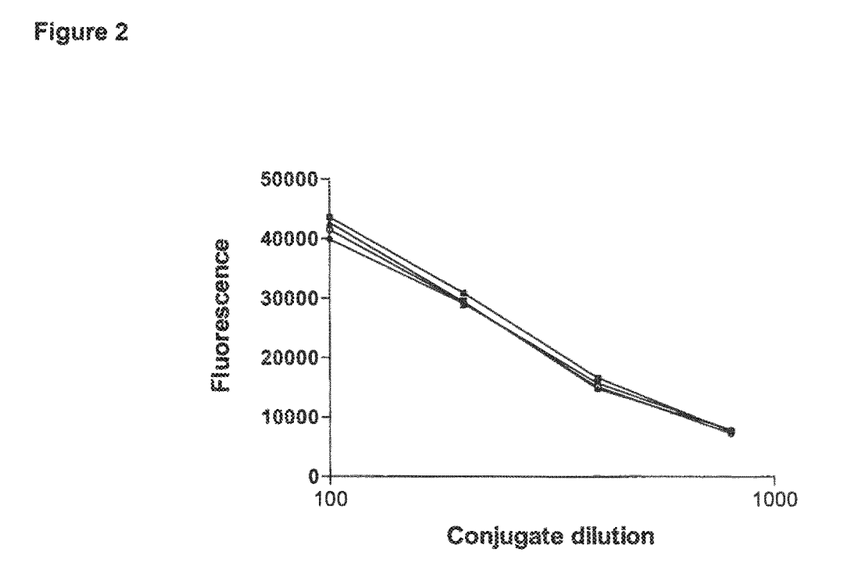
FIG. 2 shows the effect of tricine on a phycoerythrin conjugation reaction.

Tricine (a secondary amine) was evaluated in a Lightning-Link reaction with a fluorescent protein, phycoerythrin. There was a modest degree of interference in the conjugation reaction at 50 mM concentration (91% of control). Dose-response curves are shown in FIG. 2. The figure shows that there is no concentration dependent effect of tricine at various concentrations in a Lightning-Link reaction. Control (no tricine), squares; 1 mM tricine, triangles; 10 mM tricine, open circles; 50 mM tricine, closed circles.

Figure 3:
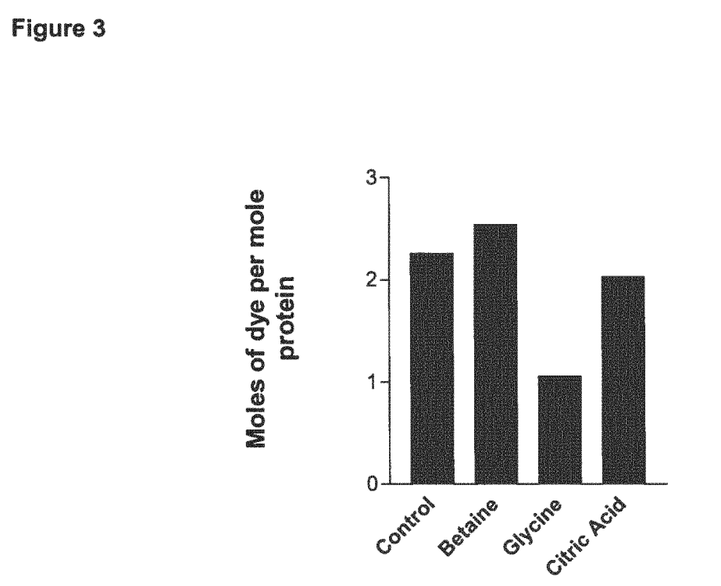
FIG. 3 shows the effect of betaine, citric acid and glycine on an isothiocyanate (fluorescein) conjugation reaction.
Figure 4:
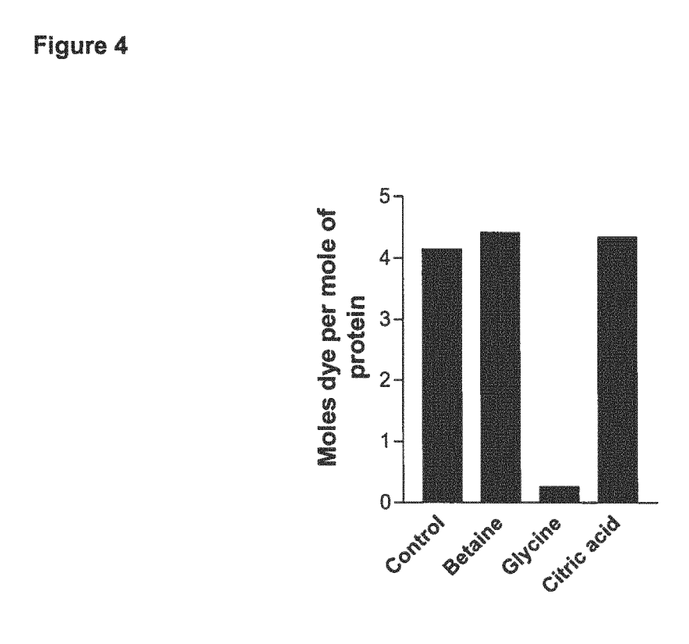
FIG. 4 shows the effect of betaine, citric acid and glycine on an NHS ester (fluorescein) conjugation reaction.

Glycine betaine was further evaluated in isothiocyanate (FIG. 3) and NHS-ester (FIG. 4) reactions and compared with the two most common buffers used in antibody purification work, glycine and citric acid. FIG. 3 shows the ratio of moles dye to moles of protein for antibody dye conjugates prepared with fluorescence isothiocyanate (FITC) in the presence of various additives. Betaine and citric acid gave results similar to that for control (no additive). Glycine showed significant interference. FIG. 4 shows the ratio of moles dye to moles of protein for antibody dye conjugates prepared with fluorescein NHS ester in the presence of various additives. Betaine and citric acid gave results similar to that for control (no additive). Glycine showed substantial interference. In contrast to its potent inhibitory effects in carbodiimide reactions (Table 1), citric acid could be tolerated in amine-dependent reactions. As expected, glycine caused significant interference, especially with NHS esters. Glycine betaine was well tolerated in both tests.

While the absence of the primary amine of glycine would prevent any competition with antibody lysines in NHS ester or isothiocyanate reactions, the resulting molecule (i.e. acetic acid) is not suitable for elution of affinity columns as the pKa of the acid group (4.76) is too high and thus it cannot act as a buffer in the required pH range. Moreover, acetic acid shows greater interference in carbodiimide reactions than glycine, despite the fact that acetic acid has a significant proportion of its carboxyls in the unreactive protonated form.

New functional groups (e.g. protected thiols) are often introduced into antibodies (and into other amine-containing substances) to extend the range of possible derivatisation reactions that can be carried out. These modifications almost always use heterobifunctional molecules with an NHS ester group at one end. Since NHS derivatives all show essentially the same reactivity with primary amines, betaine is compatible with a very wide range of popular NHS conjugation reactions.

Figure 5:
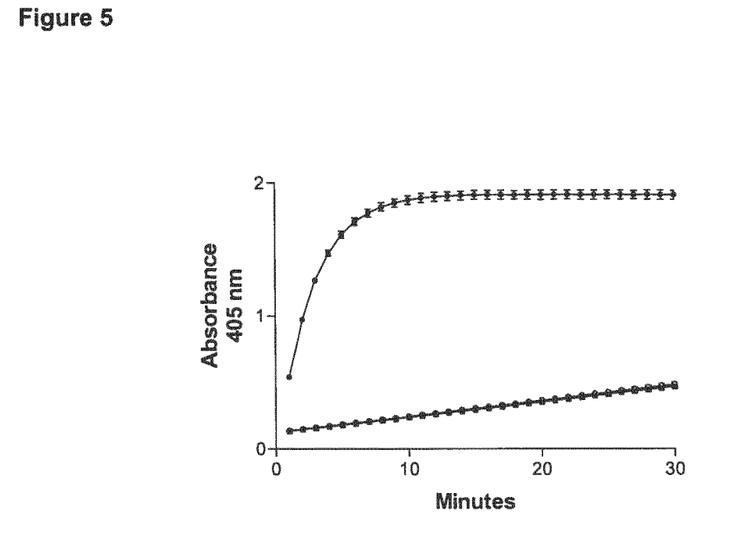
FIG. 5 shows the effect of betaine, citric acid and glycine on iminothiolane stability.

Thiols can also be incorporated directly into antibodies using non-NHS ester dependent techniques. For example, 2-iminothiolane may be used to modify lysine residues to incorporate thiol groups. FIG. 5 shows that glycine reacts rapidly with 2-iminothiolane and thus cannot be tolerated in reactions of antibodies or other amine-containing substances with 2-iminothiolane. Citric acid, as expected, had no effect on this particular amine-dependent reaction, and the quaternary ammonium compound glycine betaine again was without effect.

Other quaternary ammonium compounds are also suitable CFEBS, for example, proline betaine by analogy with glycine betaine.

Preferably primary amines have a pKa value of >9 or >10, or the pKa value should at least 1 unit or preferably 2 units above the pH of the intended conjugation reaction, so that the amine is largely protonated and relatively unreactive. Secondary amines are more preferred than primary amines, and tertiary amines are more preferred over secondary amines. Quaternary ammonium salts are particularly preferred, as the nitrogen atom retains a positive charge at all values of pH.

In affinity chromatography, in order to achieve high recoveries, columns are generally eluted between pH 2.3 and pH 3.5; most commonly the pH is pH 2.3, pH 2.8, or pH 3.0. The eluted antibody must be quickly neutralised to avoid pH-induced damage. In the case of a CFEB it is necessary only to neutralise the solution prior to conjugation (i.e. very importantly, no dialysis is required), followed later on by a further simple pH adjustment, if necessary, to meet the requirements of the particular conjugation reaction of interest.

Preferably the CFEB should have a pKa below the pH used for elution of the affinity column.

While it is traditional to use buffers at a pH value close to the pKa value, in the present invention there is a distinct advantage during the neutralisation step in not having to move through the point of maximum resistance of the CFEB to pH change, i.e. the point at which the pH equals the pKa value. The CFEB nonetheless must still be an effective buffer at the pH values at which it will be used. Generally, the useful buffering range is considered to be pKa+/−1 unit. By using a pH towards the upper end of the useful buffering range a lesser amount of neutralising buffer is required, and the neutralised antibody then has the lowest possible overall buffering capacity. This is important because subsequent conjugation reactions may be carried out at many different pH values and the intended use of the antibody may not be known when the antibody is purified and neutralised. If the solution in which the antibody is formulated has a low buffering capacity, the antibody can readily be adjusted to any new pH value by addition of a more powerful buffer.

The concentration of the CFEB should be sufficient to disrupt the binding of the antibody but no more than is absolutely necessary should be used in order to facilitate the subsequent neutralisation step. The concentration of the CFEB preferably is less than 200 mM, more preferably less than 100 mM and even more preferably less than 50 mM.

The efficiency of elution from an affinity column is determined partly by the concentration of the CFEB, as the column prior to elution typically is washed with a buffer around pH 7.5 to remove non-antibody proteins. Thus if the wash buffer is 50 mM, the transition to low pH with, for example, 10 mM CFEB will not be as abrupt as with 50 mM CFEB, as there will inevitably be some mixing of the buffers at the top of the column when the new buffer is being introduced.

Ideally, therefore, a small amount of weak buffer at around pH 7 might be used to displace a more powerful equilibration/wash buffer prior to addition of the CFEB. Alternatively, and more preferably, the column should be equilibrated and washed with a single solution of relatively low buffering capacity, prior to low pH elution. The ionic strength can be maintained, if required, even after any reduction in buffer concentration, by adding a non-buffering salt (e.g. the salt of a strong acid and strong base), such as NaCl.

In the case of small-scale antibody purifications, the column wash buffer can be largely eliminated by means of centrifuging the affinity column matrix to drive out liquid, though care should be taken not to allow the matrix to dry, which might damage the bound antibody.

In a particularly preferred embodiment of the present invention the CFEB is the quaternary ammonium compound, glycine betaine, which has a pKa of 1.8, significantly below the pH normally used to elute affinity columns (e.g. pH 2.3 and pH 2.8).

If the column is to be eluted at a higher pH (e.g. pH 3.0), an elution buffer with slightly higher pKa might be selected; for example, tricine, which has a pKa value for its carboxyl group comparable to that for glycine (pKa 2.3). Alternatively, a slightly higher concentration of a betaine such as glycine betaine could be used to maintain the required buffering capacity even though outside the normal buffering range (i.e. in the example above pH=pKa+1.2, rather than pKa+1.0).

Other substances that are used in the purification of the antibody (column equilibration buffer, wash buffer and neutralising substances) must also be compatible with the intended conjugation reaction so as not to negate the benefits of using a CFEB for elution.

While TBS (Tris-buffered saline) and PBS (phosphate-buffered saline) are commonly used as equilibration/wash buffers in affinity chromatography, neither of these is preferred in a CFEB-based antibody purification procedure, unless a pre-elution buffer displacement strategy is used. Tris interferes with amine-dependent reactions and PBS interferes with carbodiimide reactions.

However, many buffers used in biology with pKa values above 6 are suitable for use in conjugation reactions. Buffers with sulfonate groups and either piperazine or morpholino rings are commonly used and are compatible with most conjugation reactions, assuming other potentially interfering functional groups are absent from the buffer. Within a class these buffers often vary only in the number and position of methylene groups or hydroxyl substituents.

The piperazine class of buffers includes but is not limited to: (4-(2-hydroxyethyl)-1-piperazineethanesulfonic acid) (HEPES)(pKa 7.5); 3-[4-(2-Hydroxyethyl)-1-piperazinyl] propanesulfonic acid (EPPS or HEPPS)(pKa 8.0); piperazine-N,N'-bis(2-ethanesulfonic acid) (PIPES)(pKa 6.76); N-(2-Hydroxyethyl)piperazine-N'-(2-hydroxypropanesulfonic acid)(HEPPSO)(pKa 7.8); N-(2-Hydroxyethyl)piperazine-N'-(4-butanesulfonic acid) (HEPBS)(pKa 8.3).

The morpholino class of buffers includes but is not limited to: 3-Morpholino-2-hydroxypropanesulfonic acid (MOPSO) (pKa 6.9); 2-(N-morpholino)ethanesulfonic acid (MES) (pKa 6.1); 3-(N-morpholino)propanesulfonic acid (MOPS) (pKa 7.2).

Another class of buffers with relatively high pKa values includes but is not limited to the N-cyclohexyl derivatives: N-Cyclohexyl-2-aminoethanesulfonic acid (CHES)(pKa 9.5); N-cyclohexyl-3-aminopropanesulfonic acid (CAPS) (pKa 10.4); 4-(cyclohexylamino)-1-butanesulfonic acid (CABS)(pKa 10.7); 3-(cyclohexylamino)-2-hydroxyl-1-propanesulfonic acid (CAPSO)(9.6).

There are other structural variations on the above buffers and a more detailed listing may be found in Goldberg et al (J. Phys. Chem. Ref. Data, Vol. 31, No. 2, 2002)

Generally all of the above buffers are potentially useful neutralising substances and/or buffering substances and will be tolerated in most conjugation reactions. The choice of buffer or buffers will depend on the intended use of the antibody and especially the final solution pH that is required.

In one embodiment of the present invention, the buffers noted above with pKa values in the range pKa=8+/−1 units, are preferred equilibration and wash buffers. These include MOPS, HEPES, EPPS, but this selection is not limiting.

With respect to neutralisation buffers, any of the buffers noted above are potentially suitable buffers. However, the choice of buffer (or buffers, see below) must take account of the final pH that is required and the appropriateness of the pKa value(s) of the buffers.

In a preferred embodiment of the present invention the neutralising buffer has a pH above its pKa value, so that the lowest possible amount of buffer substance is required to neutralise the CFEB-containing solution of antibody. For example, a solution of EPPS buffer (pKa 8.0) could be prepared at pH 9.0. By adding a specified volume of the neutralisation buffer at a specified concentration to a specified volume of the eluted antibody in CFEB, the final pH can be engineered to be around physiological pH, still within the useful buffering range of EPPS buffer.

It is also possible to use neutralising buffers outside their useful buffering range. For example, Hepes buffer (pKa 7.5) might be used at around pH 9, assuming that great care is taken to avoid risk of overshoot when adjusting the pH in a region of very low buffering capacity. Thus the excess base (e.g NaOH) that has lifted the buffer outside its normal buffering range (i.e. pKa+/−1 unit) neutralises some of the acid in the eluted antibody, forming salt, thus minimising the mass and final concentration of actual neutralising buffer substance (i.e. in this case, Hepes).

Most antibody conjugation reactions take place between pH 5 and pH 9, because the most common reactions involve NHS esters (reactions typically at around pH 8), maleimides (around 6.5-7.5), carbodiimides (usually around pH 5-6) and thiolation reagents (typically around pH 8-8.5).

In a preferred embodiment of the current invention the neutralisation buffer comprises two buffering substances, one (the 'high pKa component') with a pKa above 8, for example preferably around pKa 9 or pKa 10, and the other one (the 'catch buffer') with a pKa of around 7.

The two components of the neutralisation buffer can be added separately or as a mixture.

Where the two components are added separately, preferably the catch buffer is added before the high pKa component to avoid overshoot to high values of pH when the high pKa component is added.

In exploratory work with a new CFEB there are advantages in doing separate additions, as the high pKa component can be added in increments and the pH measured after each addition. Subsequently, a single addition of a combined high pKa component/catch buffer solution can be made to achieve the same end point by pre-mixing the two substances in the required amounts.

Alternatively, a known volume of several potential CFEBs (or one CFEB at different pH values) can be mixed with varying volumes of each of a series of potential neutralisation buffers, and the final pH in each case can be determined and tabulated. In subsequent experiments, depending on the measured volume of the antibody in CFEB, one can refer to tables to determine which neutralisation buffer to use and how much to add to achieve the required final pH.

Upon addition of the two buffer components which results in the neutralisation of the eluted antibody, a triple buffer system is created comprising the CFEB, the high pKa component and the catch buffer (ignoring the antibody and any other buffering species present at very low concentration).

The high pKa component is likely to come from the N-cyclohexyl series of buffers, which generally have relatively high pKa values, though this is not meant to be limiting.

The pH of the neutralisation buffer is preferably above pH 7, more preferably above 8, and even more preferably somewhere between pH 8.5 and pH 11. A pH of around pH 9-9.5 is particularly useful, which is unlikely to damage the antibody upon contacting the CFEB mixture. A lower pH may of course be used in the case of antibodies that are sensitive to high pH.

If a high pKa component is used, the pH of the neutralising solution ideally is within one unit of the pKa value. If the pH is above the pKa value, a lower amount of buffer substance will be required to neutralise the CFEB than if the pH is below the pKa. However, as the high pKa component will have little buffering power at around neutral pH, the amount used to neutralise the CFEB is not particularly important and further movements in pH away from pH 7, if required, will not be resisted by the high pKa component.

When the neutralisation buffer is added to the CFEB-eluted antibody, which is typically at around pH 2.3-3.0, the mixture will become more neutral. With judicious selection of the volumes of antibody (in CFEB) and neutralising buffer, the catch buffer will be able to hold (i.e. 'catch') the pH in the range pH 6 and 8 (i.e. catch buffer pKa+/−1 pH unit).

The catch buffer, which ideally is present at the lowest possible concentration, must nonetheless be present in sufficient quantity to tolerate slight variations in the volume ratio of the CFEB solution and neutralising buffer, as may occur for example because of pipetting or measuring inaccuracies, to ensure that the pH is inside the range desirable for storage of antibodies. A final concentration around 10 mM is desirable, though this is not limiting.

If the catch buffer is added before the high pKa component the latter should be added quickly, as the catch buffer is not normally the primary neutralising substance.

After an antibody sample has been neutralised, the high pKa component originating from the neutralising solution is no longer an effective buffer. Likewise, the CFEB, which has a pKa broadly around (but preferably below) the column elution pH (i.e. in the region around pH 2.5) is not an effective buffer at pH 7. Instead the 'catch' buffer (with a pKa around 7), which is present at a relatively low concentration, provides all of the effective buffering power, but the pH of the solution can be moved relatively easily to a new pH value within the range pH 5 to pH 9 by addition of a fourth buffer (or acid or base). Even within this broad range of values neither the high pKa buffer component (assuming pKa>9, preferably 9.5 or above) nor the CFEB are particularly effective at resisting any desired change in pH.

The structural features of the catch buffer are similar to those required of the neutralisation buffers, except that ideally they should have a pKa value around pH 7. Preferably the pKa should be between pH 6 and 8, and the final pH around 7-7.5, though it may be possible to operate outside this range assuming that the antibody is stable at the chosen final pH value.

Preferred catch buffers include MOPS (pKa 7.2) and HEPES (pKa 7.5) but this is not limiting. Other buffers with similar pKa values may also be used as catch buffers.

Preferred combinations of high pKa component and catch buffer (whether added separately or together) include CHES and either MOPS or HEPES. Again, these combinations are not limiting.

Finally some amine-containing carboxylic buffers may be used, at appropriate pH values, either as CFEBs or as neutralisation buffers (e.g. tricine, and the related molecule bicine).

It will be apparent from the theory of buffers that many variant multi-component low-buffering-capacity solutions at around pH 7 can be created by combining different CFEBs with neutralising solutions comprising a high pKa component and a catch buffer. The particular components in the neutralisation buffer are not limited except that clearly none must have functional groups that interfere in the intended conjugation reactions.

Conjugation reactions using methods of the present invention consist of contacting the antibody/CFEB mixture at a suitable pH with a mixture of components comprising an activated label (or label plus activating chemicals), buffer, and other additives as required. In some cases, rather than a label, a small molecule bearing a useful functional group is attached, typically to allow the later attachment of a label via the functional group. The precise order of addition may be varied depending on the nature of the conjugation reaction, but ultimately a CFEB, catch buffer and/or neutralising buffer(s), label (or derivatisation reagent) and antibody (or protein to be labelled) are brought into simultaneous contact with one another at the start of the conjugation reaction, which is a unique aspect of the present approach. This concept was developed after the unexpected finding that amino acids, such as glycine, in certain circumstances, can be tolerated in carbodimide-mediated reactions between antibodies and nanoparticles.

In any labelling reaction, it is important that the solution of neutralised antibody, when added to a reaction, does not move the pH of the mixture away from the desired conjugation pH. Where the antibody represents a small proportion of the total reaction volume and where the buffering capacity of the antibody solution is low, the probability of a significant pH change is low. Thus an antibody formulated with a CFEB and a suitable neutralisation buffer and added in a suitable volume will be compatible with many different buffered conjugation reactions.

If the neutralised antibody is rather dilute and the volume addition would represent a significant fraction of the total assay volume, the primary buffering species in the conjugation reaction must be sufficiently concentrated to accept the antibody sample without any significant change in pH. Alternatively, the volume to be added could be reduced by increasing the antibody concentration using simple techniques well known in the art (e.g. microconcentration).

However, if the intention is to carry out only one type of conjugation reaction, the antibody in CFEB can be neutralised and adjusted directly to the required conjugation pH. In this case, no flexibility is needed to adjust the pH to other values, but there is still a major benefit in avoiding pre-conjugation dialysis steps.

For example, if the conjugation reaction is to be carried out at pH 9, the antibody can simply be adjusted to pH 9. In this scenario the use of a catch buffer with pKa of around 7 is not necessary; rather, a buffer slightly above pH 9 (and with a pKa ideally around 9) would be mixed with the eluted antibody in the required volume ratio to achieve the required final pH.

If only a portion of the antibody is to be conjugated at pH 9, it would be preferable to adjust only a portion of the antibody to pH 9, or neutralise the whole CFEB antibody solution to around pH 7 using a suitable catch buffer combined with a high pKa neutralisation buffer. The pH of a portion of the neutralised solution could then be lifted to pH 9 as and when required.

The need to neutralise eluted antibodies in a CFEB with precise volumes of neutralisation buffers is less critical when large volumes of antibody are being handled (i.e. several ml or even litres) as a pH probe can then be inserted into the solution of antibody. Desirably an alkaline buffer with an appropriate pKa (or a combination of catch buffer and high pKa component at a suitable pH) is quickly added to the CFEB without concern over the exact final pH, except that it must be sufficiently raised to minimise pH induced damage to the antibody and, preferably, the pH comes to rest at a point below the pH that ultimately is required. The final adjustment to the correct pH can then be made using a pH meter and addition of a suitable base (e.g. NaOH solution or buffer) or acid (e.g. dilute HCl) if the pH overshoots during the neutralisation step.

By careful selection of the elution buffer, its concentration, the pKa of its ionisable groups and the pH of elution buffer (especially relative to its pKa value), the antibody can easily be neutralised with a buffer or combination of buffers of higher pH (and with carefully chosen pKa values), without limiting in any way the future use of the antibody in different types of conjugation reactions.

It is also possible to elute antigen affinity columns with high pH solutions (pH>10) instead of low pH solutions. The same requirements of the CFEB apply here; the elution buffer must be compatible with the intended types of conjugation reactions. With a switch from low pH to a high pH elution strategy, the selection of a suitable neutralisation (i.e. acidic) buffer becomes more challenging, as the obvious buffers (glycine, citric acid) are not permitted with many popular conjugation chemistries. However, if non-amine dependent reactions are planned it may be possible to use citric acid as a neutralising buffer. If carbodiimide reactions are envisaged the neutralisation buffer could be low pH glycine, perhaps used along with a suitable catch buffer, though low pH glycine betaine with a catch buffer would be preferred.

N,N-dimethylglycine (amine pKa of 9.8) is a good candidate for elution of affinity columns at high pH. In this situation the neutralisation buffer might have pKa of around 7 and be added as a solution at pH 6. Either the buffer must be sufficiently concentrated to neutralise the high pH CFEB, or an acid (but in many cases not citric acid, acetic acid or low pH glycine) might be added to adjust the pH, with monitoring by means of a pH meter if possible. The buffer with a pKa of around 7 then operates as a catch buffer to prevent overshoot to very low pH values. Hydrochloric acid at a suitable concentration would be an obvious but not limiting choice of neutralising acid. Alternatively, low pH glycine betaine, preferably combined with a catch buffer of pKa ~7, as described above, could be used to neutralise a high pH solution used for elution of the affinity column.

Using methods of the present invention, mixtures of buffers with carefully selected concentrations and pKa values are simply combined with a preparation of eluted antibody in a CFEB buffer, providing a multi-component neutral solution for antibody storage, whose pH subsequently can be changed easily within the range pH 5 to 9 to suit almost any conjugation reaction. i.e. reactions involving NHS ester reactions, isothiocyanate reactions, reactions involving thiolation reagents and carbodiimide-mediated conjugation of antibodies to nanoparticles.

EXAMPLES

Example 1

Lateral Flow Assay

Lateral flow test strips (4 mm wide) were prepared from nitrocellulose membrane (Millipore Hi Flow plus 90) striped with goat anti-rabbit IgG (test line) and biotin-BSA (control line). Strips were housed in plastic cartridges and samples of gold conjugate (80 ul) were added to the sample pad. Cartridges were allowed to stand for 30 min and then read using a ESE-Quant GOLD reader—QIAGEN. Each sample was spiked with a fixed amount of streptavidin-gold (Innova biosciences—Product code: 250-0200), which binds to the control line, to check that each test strip had run correctly and that test line data was valid.

Example 2

Fluorescence Assays

Black 96-well plates (Greiner Bio-One (code 655077)) were incubated with 50 ul rabbit IgG (1 ug/well) overnight at 4° C. The plates were blocked with TBS/0.1% BSA for 1 hour at room temperature and washed five times with TBS (wash buffer). Fluorescent antibody conjugates were serially diluted in TBS/0.1% BSA and 50 ul aliquots were added to wells in triplicate. After incubation at room temperature for 1 hour, the plate was washed five times and fluorescence emission was read in using a Tecan Infinite M200 plate reader with i-Control 1.4 software with the appropriate excitation/emission settings (fluorescein, 490 nm/535 nm; phycoeythrin, 535 nm/575 nm. Fluorescence data was plotted as a function of conjugate dilution. To compare results for additives tested in different experiments the data were transformed into a percentage of a control value (i.e. the signal for conjugate prepared in the absence of any test additive).

Example 3

Conjugation Reactions with Carboxylated Gold

10 µg of goat anti-rabbit IgG (GAR) was used per ml of coated 40 nm nanoparticles with carboxyl functionality (InnovaCoat GOLD, Innova Biosciences) at 10.00 D in the presence of additives at 50 mM final concentration. Typically reactions were set up with the following additions: 40 µl of 40 nm InnovaCoat (carboxylated) gold nanopartcles, were incubated 5 minutes with 4 µl 0.1 mg/ml GAR, 20 µl water, and 80 µl of 100 mM MES buffer containing 100 mM of additive, pH 5.0. Next, 16 µl of 1 mM EDC was added and after 10 min incubation at 22° C., 20 µl of 10×TBS/1% Tween20 and 20 µl of water was added to give 2 OD conjugate.

Gold conjugates were mixed when required with rabbit IgG ((final concentration 50 ng/ml) at 22° C. Conjugates were 0.2 OD final concentration (i.e. 1/10 dilution from stock conjugates). Samples were run in triplicate on lateral flow test strips as described in Example 1.

Example 4

Effect of Various Additives on Lightning-Link Fluorescein Conjugation Reactions

Reactions were carried out according to the manufacturer's standard protocol except that the additives were included at up to 50 mM concentration in conjugation reactions of Goat-anti-rabbit IgG using fluorescein Lightning-Link kit (product code 707-0010, Innova Biosciences, UK). Conjugates were tested according to the protocol described in Example 2. Dose-response curves for conjugates prepared in the presence of glycine betaine are shown in FIG. 1, and % of control values for conjugates (1/100 dilution) prepared in the presence of the following compounds (values in parentheses) were: proline (53%), glycine betaine (98%), N,N-dimethylglycine (96%), 2 picolinic acid (83%) compared with additive-free controls (100%).

Example 5

Effect of Tricine in Light-Link Phycoerythrin Conjugation Reactions

The method was as described in Example 4, except that the Goat anti-rabbit IgG was conjugated to the fluorescent protein phycoerythrin (PE) using a Lightning-Link PE conjugation kit (703-0005). Dose-response curves for phycoerythrin conjugates prepared in the presence of tricine are shown in FIG. 2. Tricine has little effect on Lightning-Link PE conjugation reactions in the range of concentrations tested. In this case the conjugate prepared at the highest concentration of tricine (50 mM) gave a signal that was 91% of control value in the absence of additive.

Example 6

Effect of Additives on Isothicyanate Reactions

40 µg of 10 mg/ml rabbit IgG was incubated overnight in the dark at 22° C. with 50 µM FITC in 80 mM CHES buffer pH 9.0 containing 50 mM of an additive (one from glycine betaine, citric acid or glycine). Conjugates were desalted on PD10 columns (GE Healthcare) in TBS buffer and the absorbance values of the eluted solutions were determined at 280 nm and 495 nm. The ratio of moles dye to moles of protein for antibody dye conjugates in the presence of various additives is shown in FIG. 3. Glycine showed significant interference whereas glycine betaine and citric acid gave results similar to that for control (i.e. no additive).

Example 7

Effect of Additives on NHS Ester Reactions

40 µg of 10 mg/ml rabbit IgG was incubated 30 minutes in the dark at 22° C. with 50 µM Fluorescein-NHS dye in 80 mM sodium phosphate pH 8.0 containing 50 mM of one of various additives (from glycine betaine, citric acid or glycine). Conjugates were desalted on PD10 columns equilibrated in TBS buffer and absorbance values of the eluted solutions were determined at 280 nm and 495 nm. The ratio of moles dye to moles of protein for antibody dye conjugates in the presence of various additives is shown in FIG. 4. Glycine betaine and citric acid gave results similar to that for control (no additive) whereas glycine showed substantial interference Example 8

Effect of Additives on the Thiolation Reagent 2-Iminothiolane

Samples of 200 µl of 100 mM sodium phosphate pH 8.0 containing 80 ug/ml DTNB and 50 mM of additive (glycine betaine, citric acid or glycine) were added in triplicate to a clear 96-well plate (Greiner Bio-One, code 655077). 20 µl of 2 mM 2-iminothiolane was added to each well and mixed quickly and the absorbance values were read at 405 nm every minute for 30 minutes using a Tecan Infinite M200 plate reader with i-Control 1.4 software. The release of thiols from 2-iminothiolane is shown in FIG. 5. The figure shows the release of thiols in a ring opening reaction of 2-iminothiolane. In control reaction, there is a steady linear increase in absorbance as the reagent is hydrolysed by water. There is no increase in this rate in the presence of betaine or citric acid (curves superimposed with that of the control). In the presence of glycine, rapid hydrolysis and ring opening of 2-iminothiolane occurs. Neither glycine betaine nor citric acid released thiols any faster than was observed in the control reaction (no additive). The rising baseline can be attributed to the known sensitivity of 2-iminothiolane to hydrolysis at alkaline pH values.

Example 9

Use of a Catch Buffer and a High pKa Component to Neutralise a CFEB Sample

Figure 6:
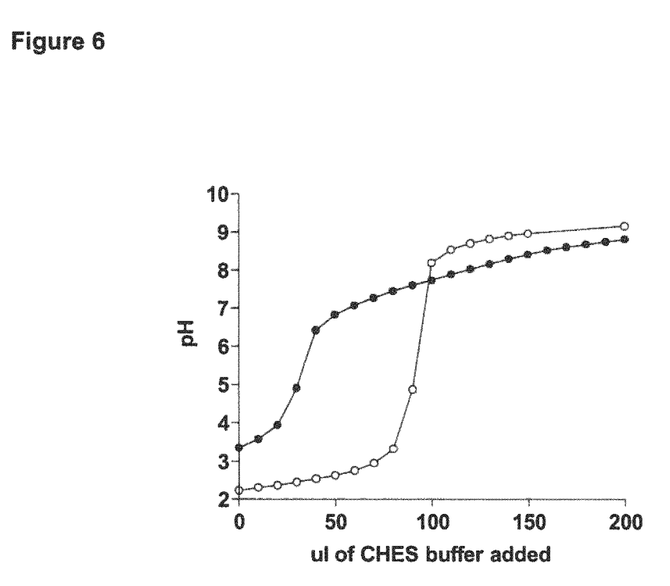
FIG. 6 shows neutralisation of CFEB with a high pKa component in the presence and absence of a catch buffer.

To 3 ml of glycine betaine, pH 2.25, was added a 'catch' buffer (30 ul of 1M Hepes, pH 7.5) followed by repeated 10 ul additions of a high pKa component (0.5M CHES buffer pH 9.5). The pH was measured after each addition. After addition of 70 ul, 80 ul and 90 ul of CHES buffer pH 9.5, the pH values of the mixture were 7.27, 7.45, and 7.6. FIG. 6 shows full pH profiles with and without the catch buffer. The figure shows the neutralisation of 3 ml of CFEB (betaine, pH 2.25) either with (solid circle) or without (open circle) catch buffer (30 ul of 1M Hepes, pH 7.5) followed by repeated 10 ul additions of 0.5M CHES buffer pH 9.5. Addition of the catch buffer raised the pH by about 1 pH unit, so the curves have different starting positions. More importantly, the catch buffer (pKa 7.5) resists changes in pH between pH 7 and pH 8 making it easy to adjust the pH to any value around pH 7.5, despite the addition of neutralisation buffer at pH 9.5. In the absence of catch buffer, an abrupt transition from pH 4.87 to pH 8.19 is seen with a single 10 ul addition (from 90 ul to 100 ul) of CHES buffer.

Example 10

Presentation Column

Goat anti-mouse Sepharose beads were packed in a disposable column (0.5 ml packed volume). After incubation with a mouse IgG-containing sample in TBS for 2 hours, the column was washed with 10 mM sodium phosphate/150 mM NaCl, pH 8.0, and then eluted with 10 mM betaine pH 2.3. Fractions of 100 ul were collected and immediately neutralised with 11.1 ul of a 10× buffer A comprising 50 mM Hepes (Catch buffer) and 90 mM CHES (high pKa component). The 10× buffer A was prepared by mixing the appropriate volumes of 1M Hepes pH 7.5, 0.5M CHES, pH 9.5, and water. The volume ratio of antibody (in betaine) to neutralisation buffer affords a final catch buffer concentration of 5 mM, and a pH of 7.1. Alternatively, the eluted fractions were neutralised with 11.1 ul of 10× buffer B (30 mM Hepes and 105 mM CHES buffer) to give a more weakly buffered preparation of antibody (i.e. catch buffer 3 mM) with a final pH of 7.55.

Purified antibodies (1 ug) were conjugated to carboxylated InnovaCoat Gold nanoparticles (Innova Biosciences) in 50 mM MES buffer, pH 5.0, and tested on lateral flow membranes striped with mouse IgG (analogous to Example 1, but with a different antibody on the test line) using goat anti-mouse IgG as a bridging reagent. Lateral flow signals were 165-277 units for conjugates from different experiments, compared with a value of 193 units for mouse IgG that had not been subjected to chromatography, and a value of zero units for controls lacking the bridging reagent.

The 50 mM MES buffer, pH 5.0, (final concentration) used in the conjugation reaction is at the extreme of its useful buffering range but was easily able to overcome the catch buffers at 3 mM and 5 mM concentration; indeed, around 40 mM MES was sufficient to reduce the pH of the two samples to pH 5.0. With a final catch buffer concentration of just 1 mM Hepes (and CHES at 10.5 mM) only 22 mM MES is required to reduce the pH to the final reaction pH of 5.0.

TABLE 1

| Additive | % of pKa Signal (COOH) | | Structure |
|---|---|---|---|
| Alanine | 100 | pKa = 2.35 | |
| DL-2 Aminobutyric Acid | 101 | pKa = 2.29 | |
| Beta-Alanine | 92 | pKa = 3.6 | |
| Glycine betaine | 96 | pKa = 1.83 | |
| Citric Acid | 0 | pKa = 3.14 | |
| Cyclohexane-carboxylic acid | 71 | pKa = 4.9 | |
| N,N-Dimethylglycine | 110 | $pKa_1$ = 2.06 | |
| GABA (γ-Aminobutyric Acid) | 26 | $pKa_1$ = 4.23 | |
| Glycine | 94 | $pKa_1$ = 2.35 | |
| N-Methylglycine (Sarcosine) | 93 | $pKa_1$ = 2.36 | |
| Na Acetate | 37 | $pKa_1$ = 4.76 | |
| Nicotinic Acid | 73 | $pKa_1$ = 2.201 | |
| 2-Picolinic Acid | 100 | $pKa_1$ = 5.52 | |

TABLE 1-continued

| Additive | % of pKa Signal (COOH) | Structure |
|---|---|---|
| Pivalic Acid | 53 pKa$_1$ = 5.03 | |
| Proline | 94 pKa$_1$ = 1.99 | |
| Succinic Acid | 0 pKa$_1$ = 4.2 | |
| TCA | 0 pKa$_1$ = 0.7 | |
| Tricine | 105 pKa$_1$ = 2.3 | |
| 2,4,6-Trihydroxybenzoic Acid | 0 pKa$_1$ = 1.68 | |
| Tris | 19 pKa$_1$ = 8.07 | |
| PBS (25 mM sodium phosphate, 150 mM NaCl) pH 7.2 | 15 | |
| 0.01% NaN3 | 26 pKa$_1$ = 4.8 | Na$^+$ N$^-$=N$^+$=N$^-$ |

The invention claimed is:

1. A method for conjugating an isolated antibody to a label or derivatisation reagent, which method comprises contacting the antibody with an activated label or activated derivatisation reagent, or contacting the antibody with the label or derivatisation reagent in the presence of an antibody conjugation reagent, in a buffer system which comprises a monocarboxylic acid buffer compound having an amine substituent at the alpha or beta position, wherein the monocarboxylic acid buffer compound is not glycine and wherein the antibody conjugation reagent, activated derivatisation reagent or activated label comprises one or more reactive groups for conjugation to the isolated antibody, the one or more reactive groups being selected from: a carbodiimide, an N-hydroxy succinimide ester, a maleimide, an isothiocyanate and a thiolation reagent.

2. A method according to claim 1, wherein the monocarboxylic acid buffer compound further comprises one or more non-amine substituents or no further substituents.

3. A method according to claim 1, wherein the amine substituent of the monocarboxylic acid is a secondary or tertiary amine, or quaternary ammonium.

4. A method according to claim 3, wherein the amine substituent is a quarternary ammonium substituent.

5. A method according to claim 4, wherein the monocarboxylic acid buffer compound is a betaine.

6. A method according to claim 5, wherein the betaine is N,N,N-trimethyl glycine.

7. A method according to claim 1, wherein the monocarboxylic acid buffer compound is a primary amino acid.

8. A method according to claim 7, wherein the primary amino acid is alanine, beta-alanine or 2-amino-butyric acid.

9. A method according to claim 8, wherein the monocarboxylic acid buffer compound is proline, tricine, N-methyl glycine, N,N-dimethylglycine or 2-picolinic acid.

10. A method according to claim 1, wherein the carboxyl group of the monocarboxylic acid buffer compound has a pKa in the range of from 1 to 4.

11. A method according to claim 10, wherein the carboxyl group of the monocarboxylic acid buffer compound has a pKa in the range of from 1.5 to 3.5.

12. A method according to claim 1, wherein the amine of the monocarboxylic acid buffer compound has a pKa of greater than 8.

13. A method according to claim 11, wherein the amine of the monocarboxylic acid buffer compound has a pKa of greater than 9.

14. A method according to claim 1, wherein the monocarboxylic acid buffer compound is present at a concentration of less than 200 mM.

15. A method according to claim 14, wherein the concentration of the monocarboxylic acid buffer compound is less than 100 mM.

16. A method according to claim 15, wherein the concentration of the monocarboxylic acid buffer compound is less than 50 mM.

17. A method according to claim 1, wherein the buffer system further comprises a neutralisation buffer compound having a pKa of greater than 5.5.

18. A method according to claim 17, wherein the neutralisation buffer compound comprises a morpholino, piperazine or N-cyclohexyl compound.

19. A method according to claim 18, wherein the neutralisation buffer compound is 2-(N-morpholino)ethanesulfonic acid (MES), 3-(N-morpholino)propanesulfonic acid (MOPS), 3-Morpholino-2-hydroxypropanesulfonic acid (MOPSO), (4-(2-hydroxyethyl)-1-piperazineethanesulfonic acid) (HEPES), 3-[4-(2-Hydroxyethyl)-1-piperazinyl]propanesulfonic acid (EPPS or HEPPS), piperazine-N,N'-bis(2-ethanesulfonic acid) (PIPES), N-(2-Hydroxyethyl)piperazine-N'-(2-hydroxypropanesulfonic acid) (HEPPSO); N-(2-Hydroxyethyl)piperazine-N'-(4-butanesulfonic acid) (HEPBS), N-Cyclohexyl-2-aminoethanesulfonic acid (CHES), N-cyclohexyl-3-aminopropanesulfonic acid (CAPS), 4-(cyclohexylamino)-1-butanesulfonic acid (CABS) or 3-(cyclohexylamino)-2-hydroxyl-1-propanesulfonic acid (CAPSO).

20. A method according to claim 17, wherein the buffer system further comprises a catch buffer compound with a pKa in the range of from 6-8, wherein the neutralisation buffer compound has a pKa above 8.

21. A method according to claim 20, wherein the pKa of the neutralisation buffer compound is in the range of from 8 to 11.

22. A method according to claim 20, wherein the catch buffer is MOPS or HEPES.

23. A method according to claim 20, wherein the concentration of the catch buffer compound is less than the concentration of the neutralisation buffer compound.

24. A method according to claim 1, wherein the label comprises an enzyme, a fluorescent protein, an organic dye, a coloured particle, biotin, streptavidin or a polymer.

25. A method according to claim 1, which is carried out at a pH in the range of from 5 to 9.

* * * * *